US005476975A

United States Patent [19]

Ruddick et al.

[11] Patent Number: 5,476,975

[45] Date of Patent: Dec. 19, 1995

[54] EXTRACTION OF TOXIC ORGANIC CONTAMINANTS FROM WOOD AND PHOTODEGRADATION OF TOXIC ORGANIC CONTAMINANTS

[76] Inventors: John N. R. Ruddick, 1365 Ottawa Avenue, West Vancouver, British Columbia, Canada, V7T 2H6; Futong Cui, 257 East 60th Avenue, Vancouver, British Columbia, Canada, V5X 1Z8

[21] Appl. No.: 272,081

[22] Filed: Jul. 8, 1994

[51] Int. Cl.[6] .......... C07C 37/68

[52] U.S. Cl. .......... 568/762; 568/761; 588/204

[58] Field of Search .......... 568/761, 762; 588/204

[56] References Cited

U.S. PATENT DOCUMENTS

| | | | |
|---|---|---|---|
| 4,308,200 | 12/1981 | Fremont | 260/110 |
| 4,338,199 | 7/1982 | Modell | 210/721 |
| 4,543,190 | 9/1985 | Modell | 210/721 |
| 4,567,115 | 1/1986 | Trumble | 428/541 |
| 4,847,002 | 7/1989 | Trumble et al. | 252/400.5 |
| 5,009,745 | 4/1991 | Hossain et al. | 162/5 |
| 5,009,746 | 4/1991 | Hossain et al. | 162/5 |
| 5,074,958 | 12/1991 | Blaney et al. | 162/5 |
| 5,213,660 | 5/1993 | Hossain et al. | 162/5 |
| 5,252,729 | 10/1993 | De Crosta et al. | 540/18 |

FOREIGN PATENT DOCUMENTS

| | | |
|---|---|---|
| 1270623 | 6/1990 | Canada . |
| 2044323 | 10/1991 | Canada . |

OTHER PUBLICATIONS

*Supercritical Carbon Dioxide Extraction of Southern Pine and Ponderosa Pine,* David C. Ritter et al, Wood and Fiber Science, Jan. 1991 V. 230 pp. 98–115.

*Effect of Fatty Acid Removal on Treatability of Douglas–Fir,* S. Kumar and J. J. Morrell, The International Research Group on Wood Preservation Process Section 4, IRG/WP 93–40008.

*Primary Examiner*—Werren B. Lone
*Attorney, Agent, or Firm*—Thomas Adams & Assoc.

[57] ABSTRACT

A process is provided herein for extracting organic toxic contaminants including pentachlorophenol, polychlorinated dibenzo-p-dioxins, and polychlorinated dibenzofurans, from wood, e.g., utility poles, fence posts, or railway ties. The process comprises extracting the wood with a supercritical fluid in conjunction with an entrainer having wood swelling properties and an agent to break the hydrogen bond between the organic toxic contaminants and the wood, at conventional supercritical fluid extraction temperatures and pressures. The process is further improved by exposing, either in a slurry of the wood phase, or in a liquid phase resulting from such extraction, the contaminants to UV, e.g., sunlight, in the presence of a photosensitizer. The present invention also provides for the photodegradation of a solution of organic toxic chemicals including pentachlorophenol, polychlorinated dibenzo-p-dioxins, and polychlorinated dibenzofurans, by exposing such solution to UV, e.g., sunlight, in the presence of a photosensitizer.

28 Claims, 6 Drawing Sheets

EXTRACTION OF TOXIC ORGANIC CONTAMINANTS FROM WOOD AND PHOTODEGRADATION OF TOXIC ORGANIC CONTAMINANTS

BACKGROUND OF THE INVENTION

(i) Field of the Invention

This invention relates to the extraction of toxic organic contaminants, e.g., pentachlorophenol, polychlorinated dibenzo-p-dioxins, and polychlorinated dibenzofurans, from treated wood, e.g., utility poles, railway ties, fence posts, etc. This invention also includes such extraction steps and the subsequent photodegradation of such extracted toxic organic contaminants. In addition, this invention relates to the photodegradation of toxic organic contaminants.

Toxic organic contaminants include polychlorinated dibenzo-p-dioxins and polychlorinated dibenzofurans, which are large groups of chloro-organic compounds which have become ubiquitous in industrial societies. Of the various possible isomers of these compounds, the following are reportedly extremely toxic: 2,3,7,8-tetrachlorodibenzo-p-dioxin, 1,2,3,7,8-pentachlorodibenzo-p-dioxin, 2,3,7,8-tetrachlorodibenzofuran, 1,2,3,7,8-pentachlorodibenzofuran, 2,3,4,7,8-pentachlorodibenzofuran, 1,2,3,6,7,8-hexachlorodibenzo-p-dioxin, 1,2,3,7,8,9-hexachlorodibenzo-p-dioxin, 1,2,3,4,7,8-hexachlorodibenzo-p-dioxin, 1,2,3,6,7,8-hexachlorodibenzofuran, 1,2,3,7,8,9-hexachlorodibenzofuran, 1,2,3,4,7,8-hexachlorodibenzofuran, and 2,3,4,6,7,8-hexachlorodibenzofuran.

Polychlorinated dibenzo-p-dioxins and polychlorinated dibenzofurans are known to cause a temporary form of a skin ailment known as "chlor-acne". Also, polychlorinated dibenzo-p-dioxins and polychlorinated dibenzofurans (particularly 2,3,7,8-tetrachlorodibenzo-p-dioxin) have been found to be extremely toxic to certain animals in laboratory studies.

Because of this reported high level of toxicity in a laboratory tests, there is a general concern as to the long-term effects of polychlorinated dibenzo-p-dioxins and polychlorinated dibenzofurans on human physiology. Accordingly, there is an important need to remove or substantially reduce the content of polychlorinated dibenzo-p-dioxins and polychlorinated dibenzofurans from used telephone poles, used railway ties, used fence posts, etc., prior to disposal or reuse of the waste. There is also a need for a process for treating solutions containing toxic organic contaminants, as described above, and including toxic organic contaminants which have been removed from treated wood, so that they can be disposed of safely.

(ii) Description of the Prior Art

Pentachlorophenol-treated utility poles contain high levels of pentachlorophenol and related contaminants, and consequently can not be disposed of in landfill sites. It has been suggested to use bioremediation as a possible way of decontaminating these materials. Poles removed from service have a high pentachlorophenol content, i.e., of the order of about 5,000–27,000 ppm in the outer 20 mm zone. This high level of pentachlorophenol is toxic to most microorganisms which have been suggested for use in the bioremediation process. Accordingly, it is necessary to pre-treat the pole material to reduce the content of such contaminants before biological remediation.

Physical or chemical methods can be used for the pretreatment process. Physical methods, e.g., dilution, i.e., mixing the pentachlorophenol-containing sawdust with large amounts of uncontaminated sawdust or other materials, so that the pentachlorophenol concentration is low enough for the microorganisms to survive, is not feasible economically. It also has the problem of generating a much larger volume of contaminated waste. Therefore, any kind of dilution approach is not considered to be suitable.

Solvent extraction is probably the easiest and most effective laboratory method of removing pentachlorophenol from contaminated wood. However, extraction using organic solvents is also not considered appropriate commercially, because of environmental concerns and the hazards involved in a large scale operation.

Chemical treatment has also been suggested for pretreating the pentachlorophenol-containing wood before bioremediation. Pentachlorophenol is, however, very stable and only a few systems can modify and/or degrade this molecule. Because of the strong, relatively non-polar covalent C-Cl bonds in pentachlorophenol, removal of the chlorine by hydrolysis is difficult. Pentachlorophenol is an electron-deficient molecule and should be more reactive towards reduction than oxidation. Potassium-graphite-intercalate has been suggested as an agent for dechlorination of a number of compounds including pentachlorophenol and octachlorodibenzo-p-dioxin. This system, however, requires inert atmosphere, high temperature and absolute anhydrous conditions and is impractical for large scale applications.

Electrochemical reduction has been suggested for use for treating waste waters containing low concentrations of chlorinated organics. Such process was considered not suitable since, for electrochemical processes to work, the electrodes must maintain clean surfaces. Moreover, the oil and other contaminants in pentachlorophenol-treated wood would contaminate the electrodes very quickly.

Reductive dechlorination of chlorinated organic compounds by photochemical reactions has also been suggested to detoxify pentachlorophenol-containing materials. Photochemical degradation of pentachlorophenol and lower chlorophenols in the presence, or absence, of various photosensitizers and catalysts have furthermore been suggested. It is known that polychlorinated biphenyls may be dechlorinated in the presence of visible dyes and amines using visible light.

Oxidation of chlorophenols by enzymes has also been suggested. Laccases may be used to remove chlorophenols from water through polymerization. This method, however, does not provide a permanent solution to the problem. The oxidation of phenolic pollutants by lignin peroxidase, an enzyme from Phanerochaete chrysosporium, has also been suggested. On the other hand, it is known that chlorophenols could be converted to much more toxic polychlorodibenzo-p-dioxins by peroxidase catalyzed oxidation.

Supercritical fluids have also been suggested to extract cellulosic materials. A supercritical fluid (SCF) is a fluid at a temperature above its critical value. An SCF has properties which are intermediate between those of gases and liquids. It has a viscosity which is lower than that of a liquid and a density which is higher than that of a gas. These properties allow SCFs to penetrate matrices easily, while retaining reasonable dissolving power. Supercritical fluid extraction (SFE) is a technique in which gases are compressed under supercritical conditions to form a fluid, which is then used to remove chemicals from a matrix. Among the various solvents suitable for SFE, carbon dioxide is the most commonly used, because it is non toxic, non-flammable, and inexpensive. Carbon dioxide also has low critical temperature and pressure, thus having a minimum requirement for equipment design. SFE provides superior extraction to routine solvent extraction in several aspects. For example, SFE leaves no solvent residue in the matrix after extraction, since carbon dioxide is a gas at normal temperature and pressure. The extract is automatically separated from the solvent when the pressure is released (carbon dioxide under noncritical conditions can hardly dissolve any of the extract), and since it eliminates the solvent-extract separation step, it is very energy efficient. In addition, SFE can be done in a closed system where carbon dioxide is continuously recycled.

Supercritical fluid technology has been applied to materials processing and pollution control. For example, it is known that supercritical ethylene may be used to remove trichlorophenol from soil. It is also known that various supercritical fluids, including carbon dioxide may be used to extract organic materials from tar sands. In addition, it is known that supercritical fluids including carbon dioxide may be used to remove hazardous organic materials from environmental solids, e.g. such as soil.

SCF extraction has been particularly useful for obtaining aromatic and lipid components from plant tissues. For example, the oil industry relies extensively on processes by which vegetable oils, e.g., soybean, cottonseed and corn oils, are removed from their vegetative components. The coffee industry uses supercritical processes for removing caffeine from coffee, and flavor extraction using SCFs has been applied to, e.g., hops, vegetables, fruits (lemons), and spices. SCF extractions have also been used to extract fragrances.

Various other uses of supercritical fluids in the processing of materials are now known. For example, supercritical carbon dioxide has been used to remove tall oil and turpentine from coniferous woods; to extract lignin from the black liquor produced by the Kraft process for pulp production; to treat refinery sludges; to regenerate absorbents used in waste water treatment systems; to sterilize pharmaceuticals; to remove off-flavor materials from textured vegetable products; to remove gamma-linolenic acid from fruit seeds; and to decaffeinate coffee; to treat citrus wastes to obtain essential oils by cooking the citrus wastes in the aqueous phase under autogenous pressure at a temperature of about 350° C. to 750° C., in the absence of air or oxygen; to extract of animal-derived materials for enzymatic treatment, e.g., endogenous and/or exogenous enzymatic treatment; for supercritical extraction of essential oils from plants with carbon dioxide for preparing pharmaceutical products; for the isolation of diosgenin, a building block for sterols from plant cell culture; and for the solubilization of biomolecules, e.g. sterols, in carbon dioxide based supercritical fluids.

Ritter et al, in paper entitled "Supercritical Carbon Dioxide Extraction of Simultaneous Pine and Ponderosa Pine", Wood and Fiber Science , Jan 1991, V.23 P.98 et seq, described the extraction of pine wood and bark using supercritical carbon dioxide. The authors also taught that the addition of ethanol to bark prior to the supercritical carbon dioxide extraction produced higher yield of extracts relative to extraction without the addition of the ethanol.

The patent literature is also replete with teachings of SFE extraction procedures. Fremont, in U.S. Pat. No. 4,308,200, taught a process for the extraction of tall oil and terpentine from coniferous woods with fluid carbon dioxide and other supercritical fluids.

Kamarei, in Canadian Patent No. 1,270,623, patented Jun. 26, 1990, provided a process for the supercritical fluid extraction of animal-derived material.

U.S. Pat. Nos. 4,338,199 and 4,543,190 to Modell, described processes in which organic materials were oxidized in supercritical water. U.S. Pat. No. 4,338,199 included a general statement that its process could be used to remove toxic chemicals from the wastes generated by a variety of industries including forest product wastes and paper and pulp mill wastes. U.S. Pat. No. 4,543,190 described the treatment of various chlorinated organics other than dioxins with supercritical water and stated that conversion of these materials to chlorinated dibenzo-p-dioxins were not observed.

U.S. Pat. No. 5,009,746, patented Apr. 23, 1991 by Hossain et al, provided a method for removing polychlorinated dibenzofurans from secondary fibers by contacting the secondary fibers with supercritical or near supercritical carbon dioxide for a period of time at a temperature, pressure, and carbon dioxide flow rate such that a substantial reduction in the level of polychlorinated dibenzofurans associated with the fibers was achieved, and the properties of the fibers, e.g., their physical and chemical properties, were not substantially degraded. The operating conditions taught included: the use of pressures above about 60 atmospheres; temperatures above about 25° C.; carbon dioxide flow rates in the range from about 0.01 standard liters/minute/gram of dry secondary fiber (slpm/gm) to about 10 slpm/gm; and processing periods of from about 1 minute to about 3 hours.

U.S. Pat. No. 5,009,746, patented Apr. 23, 1991 by Hossain et al, provided a method for removing stickies from secondary fibers by contacting the secondary fibers with supercritical or near supercritical carbon dioxide for a period of time at a temperature, pressure, and carbon dioxide flow rate such that a substantial reduction in the level of stickies associated with the fibers was achieved, and the properties of the fibers, e.g., their physical and chemical properties, were not substantially degraded.

U.S. Pat. No. 5,074,958, patented Dec. 24, 1991 by Blaney et al, provided a method for removing polychlorinated dibenzofurans from secondary fibers by contacting the secondary fibers with supercritical or near supercritical carbon dioxide or propane for a period of time at a temperature, pressure, and carbon dioxide or propane flow rate such that a substantial reduction in the level of polychlorinated dibenzofurans associated with the fibers was achieved, and the properties of the fibers, e.g., their physical and chemical properties, were not substantially degraded. That patent also taught a method for removing stickies from secondary fibers by contacting the secondary fibers with supercritical or near supercritical carbon dioxide or propane for a period of time at a temperature, pressure and carbon dioxide or propane flow rate such that a substantial reduction in the level of stickies associated with the fibers was achieved, and the properties of the fibers, e.g., their physical and chemical properties, were not substantially degraded.

U.S. Pat. No. 5,213,660, patented May 25, 1993 by Hossain et al, provided a method for removing polychlorinated dibenzofurans from secondary fibers by contacting the secondary fibers with supercritical or near supercritical carbon dioxide for a period of time at a temperature, pressure, and carbon dioxide flow rate such that a substantial reduction in the level of polychlorinated dibenzofurans associated with the fibers was achieved, and the properties of the fibers, e.g., their physical and chemical properties, were not substantially degraded.

It is now known that the solubility of various chemicals in supercritical carbon dioxide is directly related to the temperature and pressure being used, as well as to the presence of different co-solvents, called "entrainers". It is known that the extraction efficiency and selectivity can be optimized by adjusting these parameters, i.e., temperature, pressure and entrainers.

Kumar et al, in a paper entitled "Effect of Fatty Acid Removal in Treatability of Douglas Fir", presented to The International Research Group on Wood Preservation, Section 4, "Process", Document No. IRG/WP 93-40008, reported on the extraction of fatty acids using supercritical carbon dioxide. The extraction was carried out using supercritical carbon dioxide and methanol or methanol and formic acid as co-solvents. The authors suggested that the addition of co-solvents in supercritical carbon dioxide extraction increases the solventing properties of the supercritical fluid.

Following up on these general teachings, U.S. Pat. No. 5,252,729, patented Oct. 12, 1993 by De Crosta et al, provided two extraction processes. One process was for extracting a compound from plant material by contacting hydrolyzed plant material with a supercritical fluid, optionally with a co-solvent, and recovering the compound from the supercritical fluid. A second process was for removing a compound from plant material, by contacting the plant material with an acid, a supercritical fluid and a co-solvent, and recovering the compound from the supercritical fluid.

That patentee also taught that the hydrolyzed plant material can be prepared by treatment of fresh or dried plant material with acid under conditions effective to promote hydrolysis. Useful acids for hydrolyzing the plant material taught by such patentee included mineral acids, e.g., sulfuric acid, hydrochloric acid, or phosphoric acid, or organic acids, e.g., formic acid, acetic acid, propanoic acid, butyric acid, o-, m- or p-toluene sulfonic acid, benzoic acid, trichloroacetic acid, trifluoroacetic acid; or mixtures of any of the above acids.

That patentee also taught that, optionally, a base could be added during or at the completion of hydrolysis of the root to neutralize any excess acid. Suitable bases, as taught by that patentee, included hydroxides, carbonates and bicarbonates of an alkali metal, e.g., sodium, lithium, or potassium, or of an alkaline earth metal, e.g., calcium or magnesium.

That patentee further taught that representative extracting (solvating) mobile phase components includes the elemental gases, e.g., helium, argon, nitrogen, and the like; inorganic compounds, e.g., ammonia, carbon dioxide, water, and the like; organic compounds, e.g., $C_1$ to $C_5$ alkanes or alkyl halides, e.g., monofluoro methane, butane, propane carbon tetrachloride, and the like; or combinations of any of the above.

The patentee also taught that the supercritical fluid could be modified by the addition of inorganic and/or organic modifiers, e.g., compounds as listed above. The patentee taught that the most preferable supercritical fluid was carbon dioxide admixed with chloroform.

That patentee further taught the use of a co-solvent which should be compatible with the supercritical fluid selected and should also be capable of at least partially dissolving the compound being extracted. Suitable co-solvents for use in conjunction with the supercritical fluid as taught by that patentee included aromatics, e.g., xylene, toluene and benzene; aliphatics, e.g., $C_5$ to $C_{20}$ alkanes including hexane, heptane and octane; water; $C_1$ to $C_{10}$ alcohols, e.g., methanol, ethanol, propanol, butanol and isopropanol; ethers; acetone; chlorinated hydrocarbons, e.g., chloroform, carbon tetrachloride or methylene chloride; or mixtures of any of the above. The co-solvent was said to be employed in amounts effective to aid in the wetting and/or hydrolysis of the plant material, and can range from excess to about one volume of solvent per one volume of acid, preferably from about 10 to one volume of solvent per one volume of acid.

The operating conditions taught by that patentee included the contacting with the supercritical fluid at temperatures ranging from about 30° C. to about 300° C., preferably from about 75° C. to about 250° C. The pressure employed was said to be sufficient to maintain the supercritical fluid, and was said to be able to be increased from ambient atmospheric pressure to about 400 atmospheres or more, preferably between about 100 and 300 atmospheres.

Accordingly, it would appear that fluid extraction using supercritical fluid (SFE) should be a viable procedure for reducing the toxic chemicals present in the wood, e.g., waste wooden pole materials and used railway ties. It has been found, however, that the extraction of toxic chemicals from wood, e.g., utility poles and used railway ties is not very efficient.

It is thought that the degradation of pentachlorophenol, polychlorinated dibenzo-p-dioxins and polychlorinated dibenzofurans in solution and in sawdust slurry may be achieved by photochemical reactions. However, a commercially-viable such photochemical degradation has not been taught by the prior art.

SUMMARY OF THE INVENTION (i) Aims of the Invention

Accordingly, it is an object of the present invention to provide a process for increasing the extraction efficiency of contaminants from wood using a supercritical fluid.

Another object of this invention is to provide a process for the photodegradation of such extracted contaminants.

Yet another object of this invention provides a process for the photodegradation of chlorinated organics without separation from the contaminated material.

(ii) Statement of Invention

The present invention now provides a process for extracting contaminants from wood, e.g., utility poles, railway ties, fence posts, etc., such contaminants including pentachlorophenol, polychlorinated dibenzo-p-dioxins and polychlorinated dibenzofurans, etc., which process comprises: extracting such contaminant-containing wood with a supercritical fluid (e.g., carbon dioxide) and an entrainer having wood swelling properties (e.g., water and/or methanol) and an agent, (e.g., sodium fluoride), to break the hydrogen bond between the contaminants mentioned above and the wood, at conventional supercritical fluid extraction temperatures and pressures, thereby to extract such contaminants from the wood.

The present invention also provides a process for extracting contaminants from wood, e.g., utility poles, railway ties, fence posts, etc., such contaminants including pentachlorophenol, polychlorinated dibenzo-p-dioxins, and polychlorinated dibenzofurans, etc., and the subsequent photodegradation of the extracted contaminants which process comprises: extracting such contaminant-containing wood with a supercritical fluid (e.g., carbon dioxide) and an entrainer having wood swelling properties (e.g., water and/or methanol) and an agent, (e.g., sodium fluoride), to break the hydrogen bond between the contaminants mentioned above and the wood, at conventional supercritical fluid extraction temperatures and pressures; and exposing, in a slurry of the extracted wood or in a liquid solvent phase resulting from the extraction, the contaminants to radiation including UV or sunlight, in the presence of a photosensitizing amount of a suitable photosensitizer (e.g., methylene blue or protoporphyrin IX).

The present invention also provides a process for photodegrading organic toxic chemicals including pentachlorophenol, polychlorinated dibenzo-p-dioxins, and polychlorinated dibenzofurans in a solution thereof which process comprises: exposing the solution to radiation including UV or sunlight, in the presence of a photosensitizing amount of a suitable photosensitizer.

(iii) Other Features of the Invention

By one feature of one embodiment of the invention, the supercritical fluid is carbon dioxide.

By another feature of this embodiment of the invention, the entrainer is water, methanol, ethanol, propanol, isopropanol, toluene, acetone, tetrahydrofuran, dimethylformamide or dimethylsulfoxide.

By yet another feature of this embodiment of this invention, the hydrogen-bond-breaking agent is an alkali metal fluoride, preferably lithium fluoride, or potassium fluoride or sodium fluoride.

By still another feature of the invention, the wood, prior to the supercritical fluid extraction may be reduced in size by one of the following alternative procedures: comminuting the wood; or chipping the wood; or forming flakes from the wood; or producing segments from outer sapwood of treated utility poles, and reducing such segments to flakes; or producing thin sheets of wood from outer sapwood of treated utility poles.

By a feature of the photodegradation embodiments of this invention, the radiation comprises direct sunlight.

By another feature of this embodiment of this invention, the suitable photosensitizer may be methylene blue, various porphyrins, e.g., etioporphyrin, or protoporphyrin IX, or various phthalocyanines, e.g., phthalocyanine, 2,3-naphthalocyanine.

By a further feature thereof, the solvent providing the solution is acetonitrile, methanol, ethanol, or other water-miscible solvents.

By yet another feature thereof, the process takes place in the presence of an amine, e.g., triethanolamine.

By yet other features thereof, the photodegradation to degrade the toxic organic contaminants may take place in a slurry of the contaminated wood, or the photodegradation to degrade toxic organic chemicals may take place in a liquid solvent phase.

BRIEF DESCRIPTION OF THE DRAWINGS

In the accompanying drawings.

DESCRIPTION OF PREFERRED EMBODIMENTS

Before describing Examples of this invention, Applicant wishes to set forth certain general features of the process.

CHEMICALS USED

All the chlorophenol and dihydroxychlorobenzene standards were obtained from Fluka. Pentachlorophenol was 99% pure from Aldrich and was used without further purification. Technical grade pentachlorophenol, manufactured by KMG, was provided by a preservative treating plant. Methylene blue double zinc salt, was acquired from Matheson, Coleman and Bell. Phthalocyaninetetrasulfanate sodium salt was purchased from Porphyrin Products. Protoporphyrin IX was a gift from Professor David Dolphin, Department of Chemistry, UBC. Triethanolamine (99.8%, certified) was purchased from Fisher Scientific. All solvents were spectral grade (OMNISOLVT$_{TM}$) from BDH and all other chemicals were of analytical grade.

GENERAL PROCEDURE

One general procedure adopted was to produce segments from the treated wood (generally the outer sapwood). While many ways are possible to produce the segments, one procedure is to produce the segments by a saw. These segments are reduced to flakes. It has been found that the use of the flakes in the SCF extraction process facilitated the process.

However, it is possible that pole sections could be used without any processing apart from reduction of length. It is also possible that the poles could be peeled to produce veneer. Moreover, it may be possible to use the SCF extraction process without processing the wood, as well as after peeling to produce veneer or flakes for OSB or waferboard.

EQUIPMENT USED

The supercritical fluid extractor was a HP 1081B modified apparatus. The GCMS was a VG Trio-1000 system equipped with a 30 meter DB-5 column. The reagent gas for chemical ionization (CI) GCMS was ultra high purity methane. GC-ECD (electron-capture detector) was carried out on a HP 5890 II GC with a 30 meter DB-1 column. Sample injection for the GC-ECD was done by using a HP 7670 autosampler.

SUPERCRITICAL FLUID EXTRACTION PROCEDURE

The equipment used was a Hewlett-Packard 1081B modified SFE apparatus with a 40 mL extraction chamber. Liquid carbon dioxide was constantly introduced into the extraction chamber by a high pressure pump, at a constant flow rate. The extraction chamber was connected to a pressure valve, which opened when the pressure exceeded the required pressure. The wood samples were pre-treated for 24–48 hours with the solvents which were to be used as entrainers. Pentachlorophenol-treated pole material to be extracted was ground into 30 mesh powder and loaded into the extraction chamber. The pentachlorophenol retention of the wood prior to, and after extraction, was determined by the X-ray fluorescence analysis. The results presented are the average of three runs.

EXAMPLE 1

Prior Art Extraction of Pentachlorophenol

Figure 1:
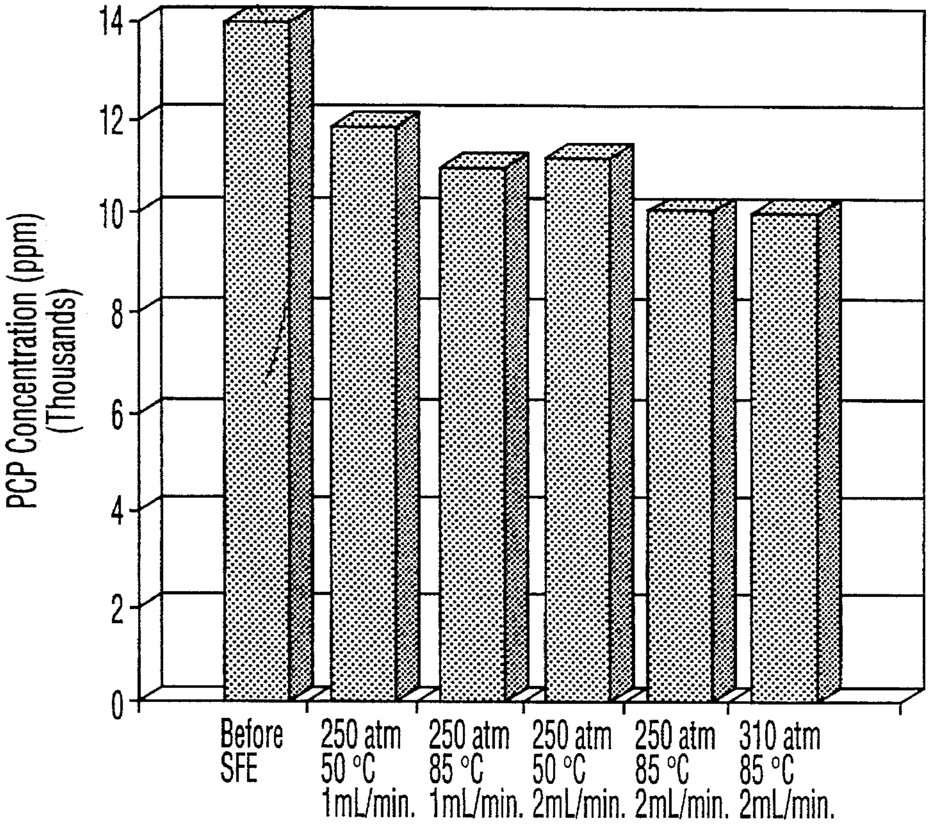
FIG. 1 is a bar graph depicting supercritical carbon dioxide extraction of pentachlorophenol-containing jackpine sapwood (0–20 mm layer) for one hour under various conditions, in which the ordinate is pentachlorophenol concentration (ppm, thousands)

This example represents a version of the prior art extraction of pentachlorophenol from the sawdust of a jackpine pole, which was treated in 1974. The bar graph of FIG. 1 shows supercritical carbon dioxide extraction of sapwood from the jackpine (0–20 mm layer) under various conditions. The SFE of pentachlorophenol from treated jackpine sapwood, using carbon dioxide as the solvent, was not very efficient, as can be seen from FIG. 1. Varying the temperature, pressure, and flow rate had little effect on the extraction efficiency, in the ranges studied. While it is not desired to be limited by theory, it is thought that the low extraction efficiency may be caused by low solubility of pentachlorophenol in the supercritical solvent. Alternatively, while it is not desired to be limited by theory, it is thought that a strong interaction between pentachlorophenol and the wood matrix may inhibit the extraction process. The fact that increasing the solvent flow rate from 1 mL/minute to 2 mL/minute did not result in a significant pentachlorophenol reduction (FIG. 1), suggested that a strong interaction between pentachlorophenol and wood matrix was the more important factor.

EXAMPLE 2

Extraction of Pentachlorophenol in the Presence of Entrainers and Fluoride Salts The effect of various entrainers on the extraction efficiency of pentachlorophenol from the 0–20 mm and the 20–40 mm zones of a 1974 jackpine pole after one hour extraction at 50° C. and 250 atmosphere with a solvent flow rate of 1 mL/minute with and without entrainers (4 mL), extraction time: 1 hour, or otherwise as specified, were investigated.

Figure 2:
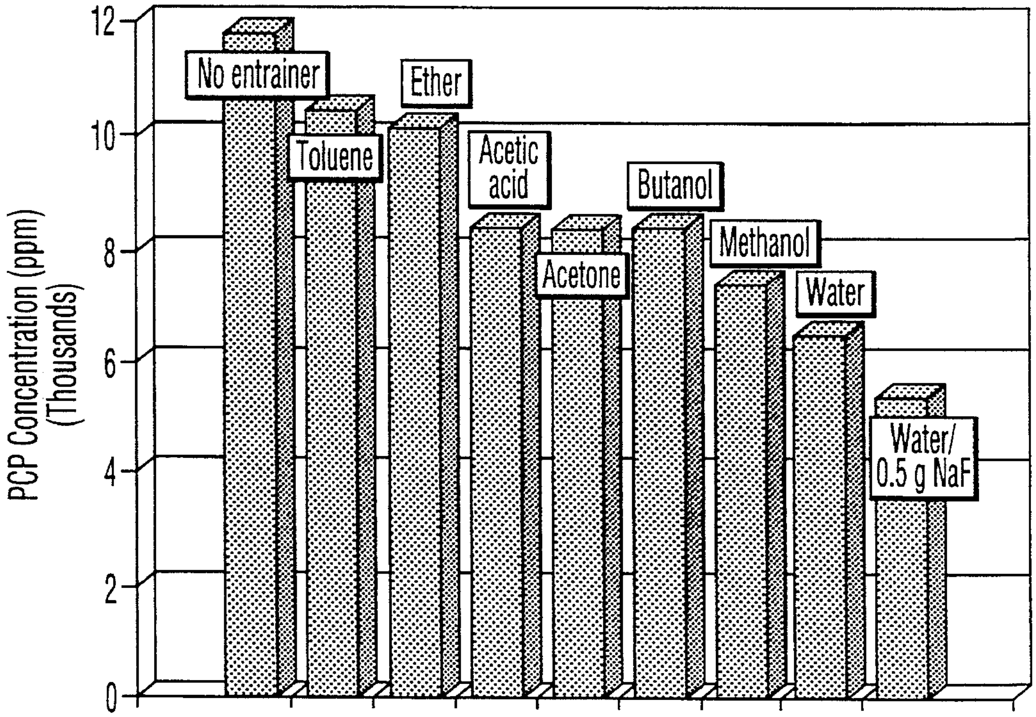
FIG. 2 is a bar graph depicting the effect of various entrainers on the extraction efficiency of pentachlorophenol from the 0–20 mm zone of a jackpine pole after one hour extraction at 50° C. and 250 atmosphere with a solvent flow rate of 1 mL/minute, in which the ordinate is pentachlorophenol concentration (ppm, thousands)
Figure 3:
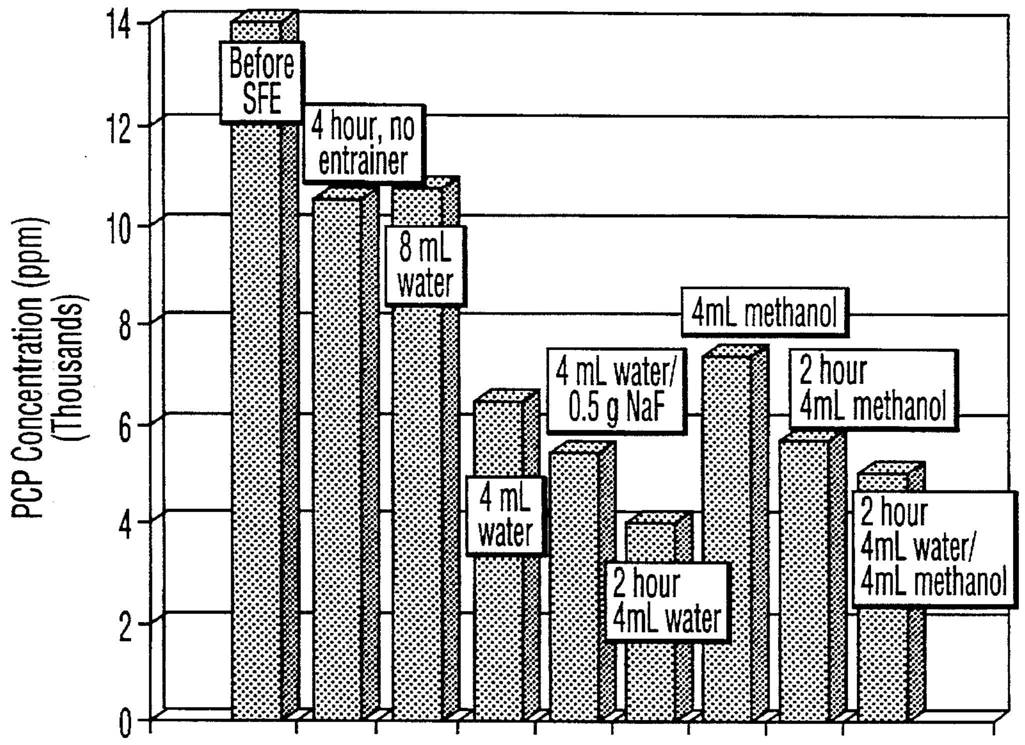
FIG. 3 is a bar graph depicting the supercritical fluid extraction of the 0–20 mm zone of a jackpine pole under various conditions, extraction temperature: 50° C., pressure: 250 atmosphere, solvent flow rate: 1 mL/min., extraction time: for 1 hour or otherwise as specified, in which the ordinate is pentachlorophenol concentration (ppm, thousands)

The extraction was enhanced by all the solvents tested (FIGS. 2 and 3). Water, which is not usually a good solvent for pentachlorophenol was found to be a moderately efficient entrainer (FIG. 2).

Figure 4:
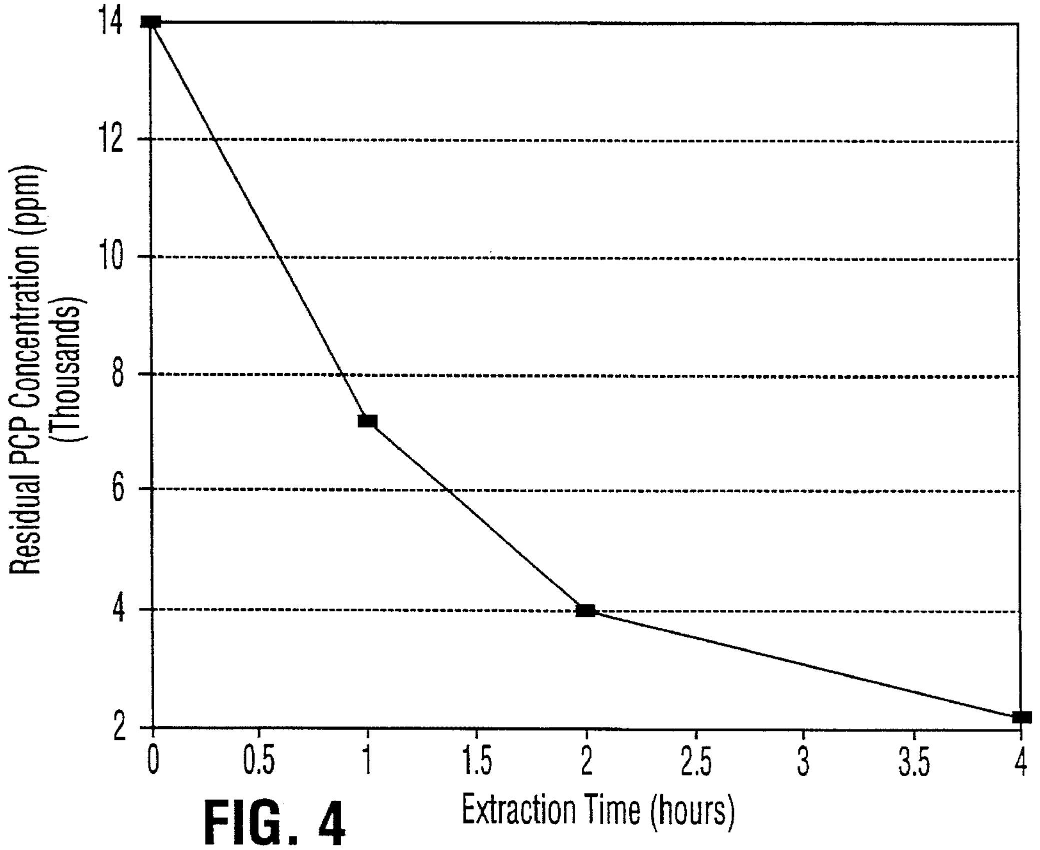
FIG. 4 is a graph depicting the residual pentachlorophenol concentration as a function of extraction time, jackpine sapwood pre-treated with 4 mL water, extracted at 50° C., 250 atm., and 1 mL/min. solvent flow rate, in which the ordinate is residual pentachlorophenol concentration (ppm, thousands)

FIG. 4 shows the effect of extraction time on the residual pentachlorophenol concentration of wood pretreated with water. The pentachlorophenol content was reduced by 50% in the first hour of extraction. The extraction of the remaining pentachlorophenol was more difficult, and 15% pentachlorophenol remained after 4 hours of extraction.

While it is not desired to be bound by theory, it is believed that the most plausible explanation for this behaviour is that water swells wood, thereby opening the structure and making it easier for the solvent to penetrate into the matrix. Water interacts with lignin and cellulose in the wood, thereby forming hydrogen bonding, and thus weakening the previous pentachlorophenol-wood interaction. Addition of sodium fluoride to water further improved its efficiency as an entrainer, since it has been found that fluorides will destroy hydrogen bonding between pentachlorophenol and lignin or cellulose.

While it is not desired to be bound by theory, it is believed that the organic entrainers probably increased the extraction efficiency by increasing pentachlorophenol solubility, by destroying hydrogen bonds between pentachlorophenol and wood and by swelling the wood.

EXAMPLE 3

Extraction of Dioxins in the Presence of Entrainers

The changes of total polychlorodibenzo-p-dioxin concentration and octachlorodibenzo-p-dioxin concentration in 1974 jackpine pentachlorophenol-treated pole material after supercritical fluid extraction under various conditions, all extractions being carried out at 50° C. and 250 atmosphere, were investigated.

Figure 5:
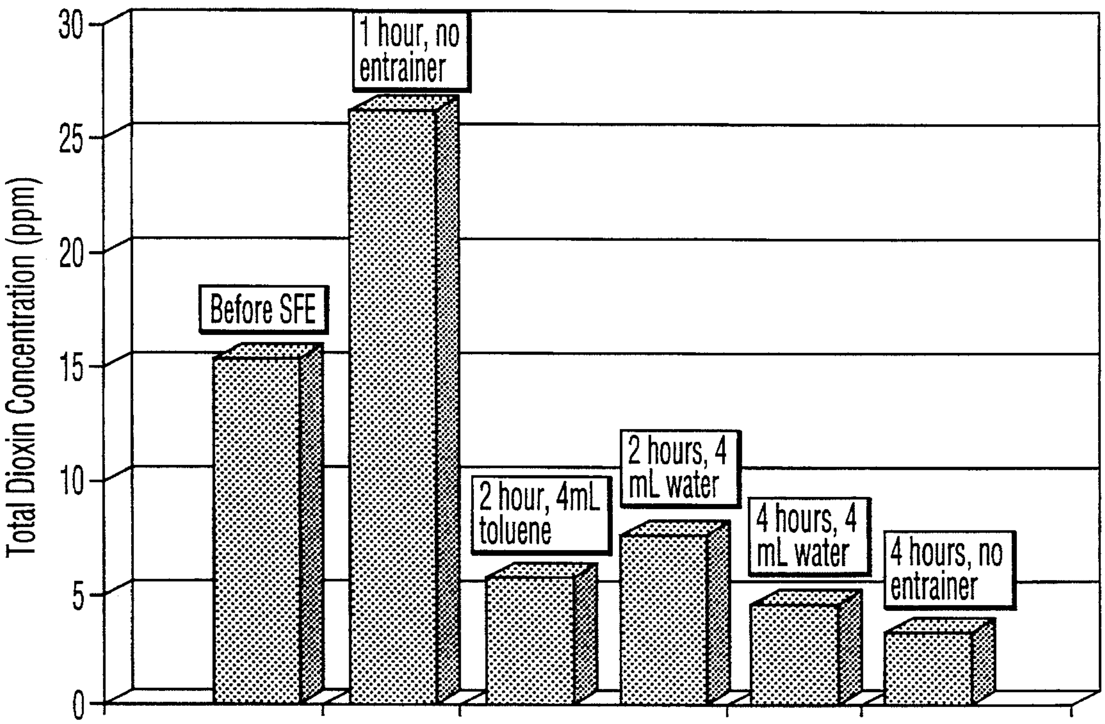
FIG. 5 is a bar graph depicting the change of total polychlorodibenzo-p-dioxin concentration after supercritical fluid extraction under various conditions, all extractions being carried out at 50° C. and 250 atmosphere, in which the ordinate is total polychlorodibenzo-p-dioxin concentration (ppm)

As shown in FIG. 5, with one exception, total dioxin content decreased after extraction in all cases. The total dioxin content increased after SFE for one hour at 50° C. and 250 atmosphere without an entrainer. This was unexpected, since dioxin formation from precursors was virtually impossible under these conditions. After four hours of extraction without entrainer, the total dioxin content decreased by 80%.

Figure 6:
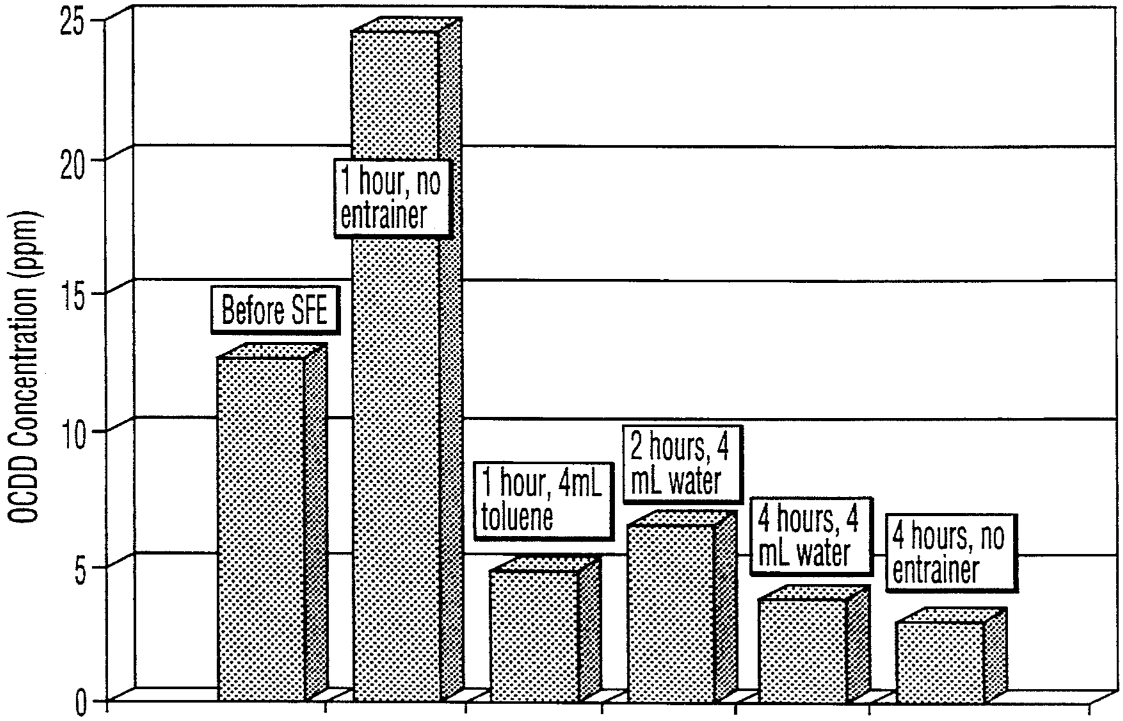
FIG. 6 is a bar graph depicting the change of octachlorodibenzo-p-dioxin concentration after supercritical fluid extraction under various conditions, all extractions being carried out at 50° C. and 250 atmosphere, in which the ordinate is octachlorodibenzo-p-dioxin concentration (ppm)

As also shown in FIG. 5, a four hour extraction using water as the entrainer was less effective than that without entrainer. Toluene, on the other hand, was quite an effective entrainer. After only one hour of extraction using toluene as the entrainer, the total dioxin content decreased by over 60%. The decrease in octachlorodibenzop-dioxin content after SFE under various conditions was similar to that for the total dioxin as shown in FIG. 6.

The change of total heptachlorodibenzo-p-dioxin concentration after supercritical fluid extraction under various conditions, and the change of total hexachlorodibenzo-p-dioxin concentration after supercritical fluid extraction under various conditions, where all extractions were carried out at 50° C. and 250 atmosphere, were all investigated.

Figure 7:
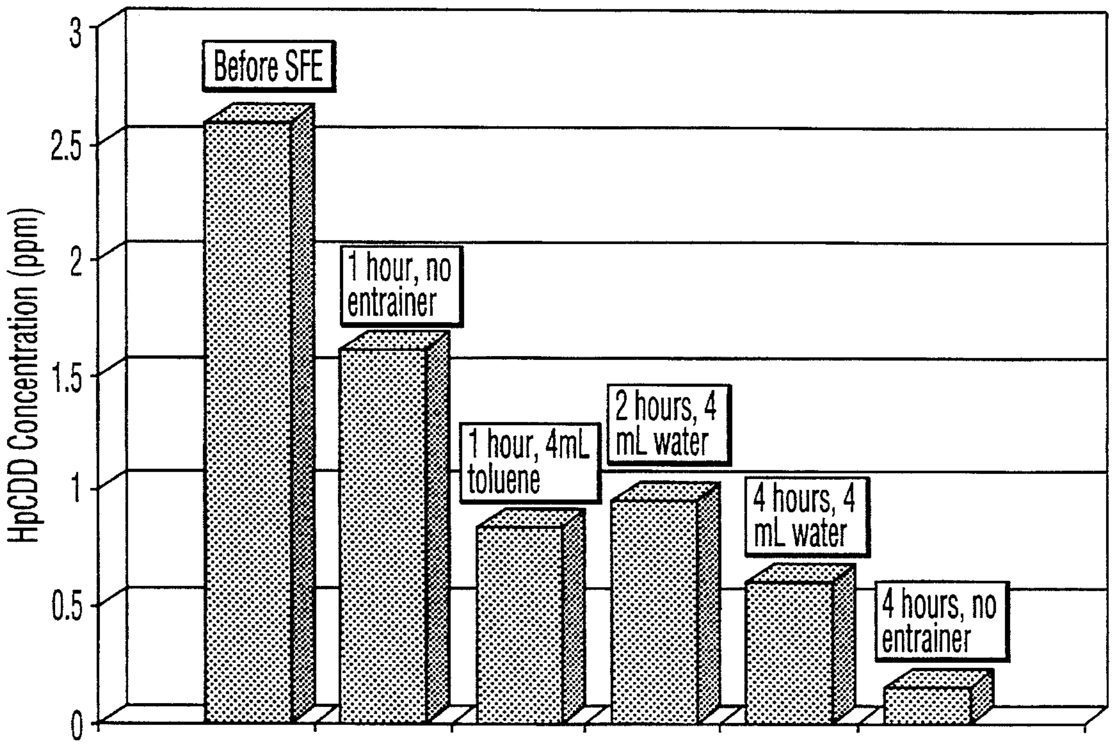
FIG. 7 is a bar graph depicting the change of total heptachlorodibenzo-p-dioxin concentration after supercritical fluid extraction under various conditions, all extractions being carried out at 50° C. and 250 atmosphere, in which the ordinate is heptachlorodibenzo-p-dioxin concentration (ppm)
Figure 8:
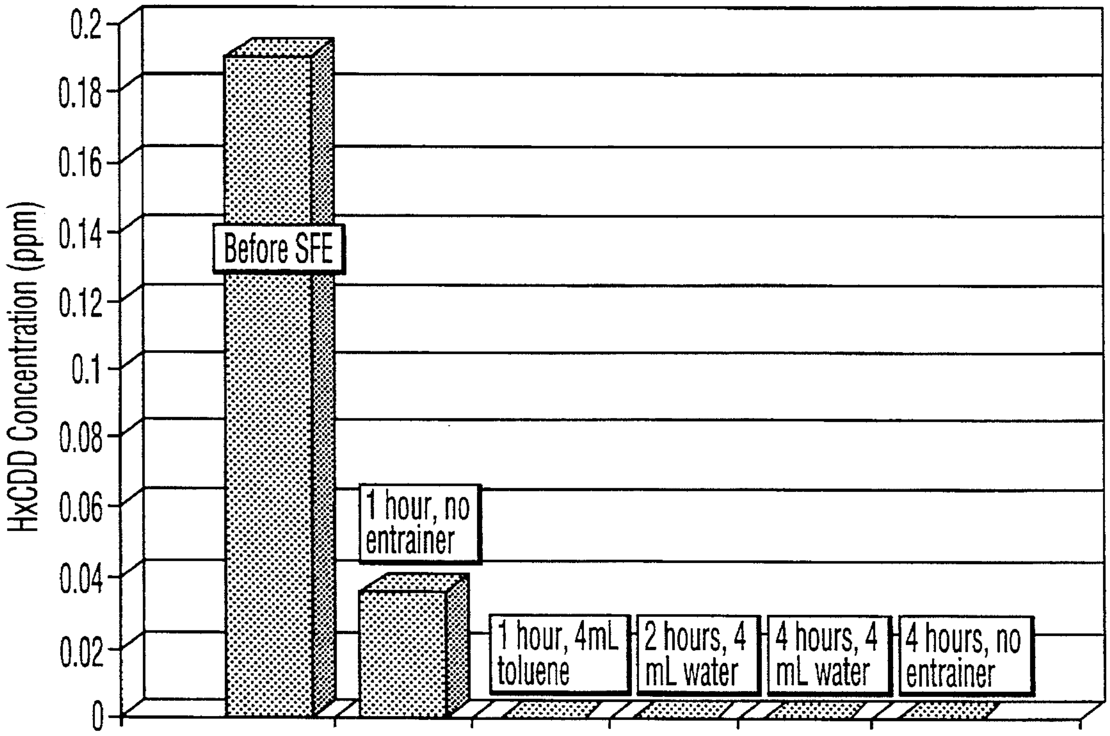
FIG. 8 is a bar graph depicting the change of total hexachlorodibenzo-p-dioxin concentration after supercritical fluid extraction under various conditions, all extractions being carried out at 50° C. and 250 atmosphere, in which the ordinate is hexachlorodibenzo-p-dioxin concentration (ppm)
Figure 9:
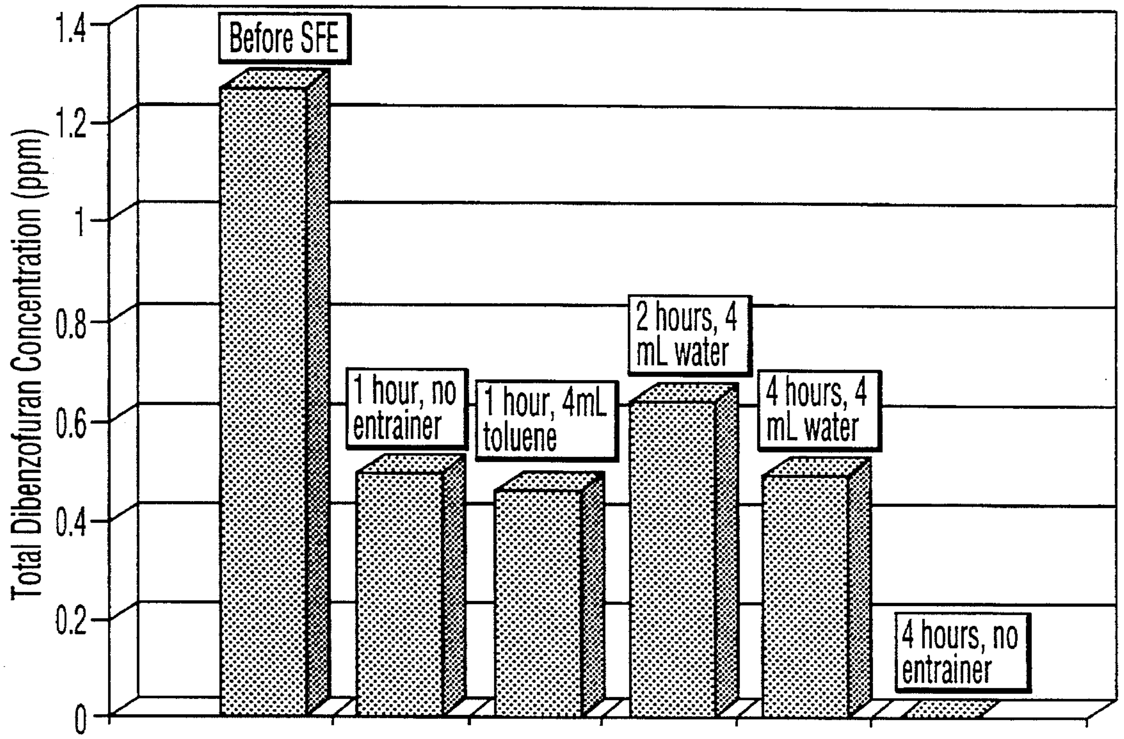
FIG. 9 is a bar graph depicting the change of total polychlorodibenzofuran concentration after supercritical fluid extraction under various conditions, all extractions being carried out at 50° C. and 250 atmosphere, in which the ordinate is total dibenzofuran concentration (ppm)
Figure 10:
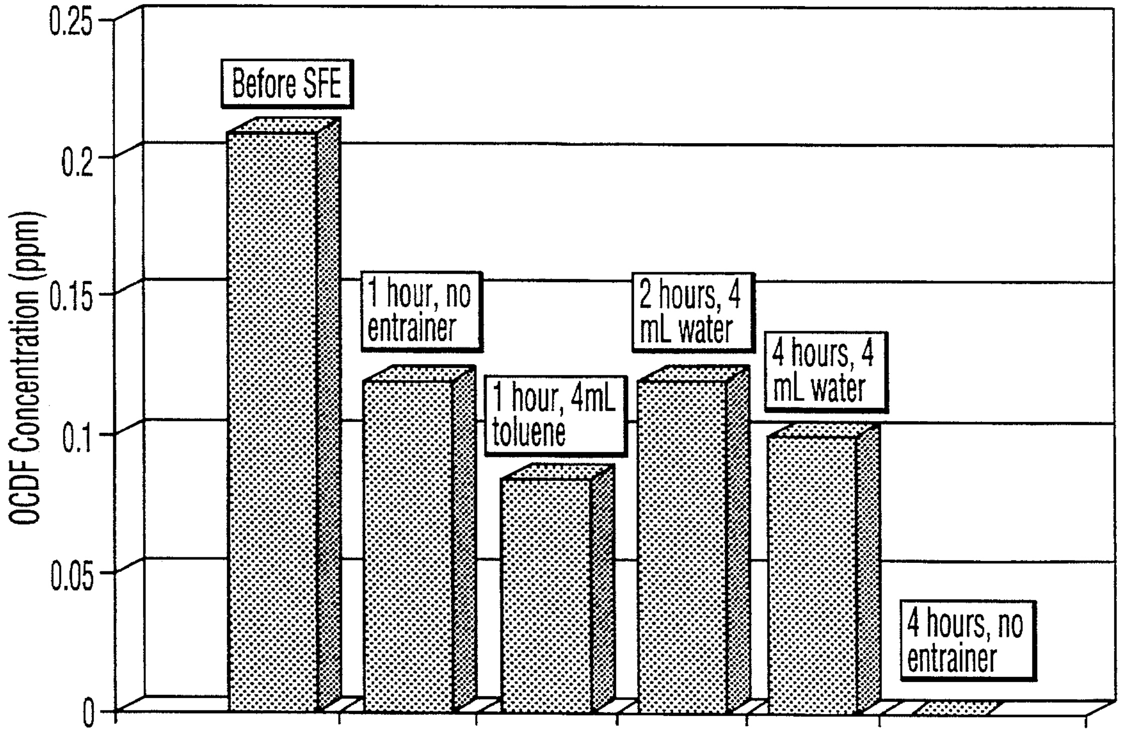
FIG. 10 is a bar graph depicting the change of octachlorodibenzofuran concentration after supercritical fluid extraction under various conditions, all extractions being carried out at 50° C. and 250 atmosphere, in which the ordinate is octachlorodibenzo-p-dioxin concentration (ppm)
Figure 11:
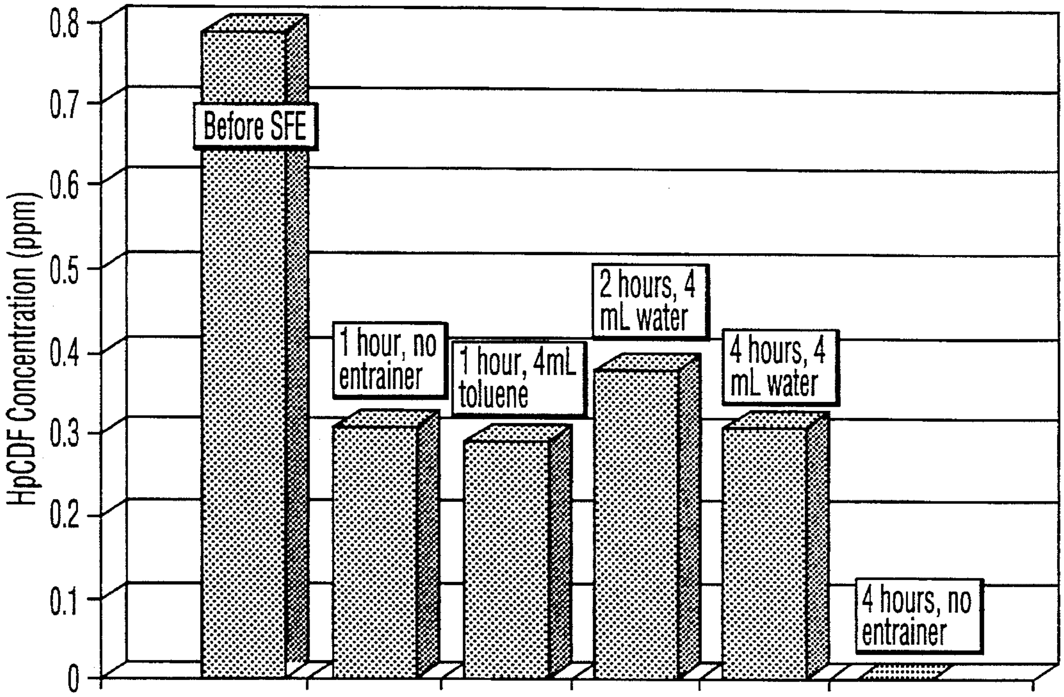
FIG. 11 is a bar graph depicting the change of total heptachlorodibenzofuran concentration after supercritical fluid extraction under various conditions, all extractions being carried out at 50° C. and 250 atmosphere, in which the ordinate is heptachlorodibenzofuran concentration (ppm)
Figure 12:
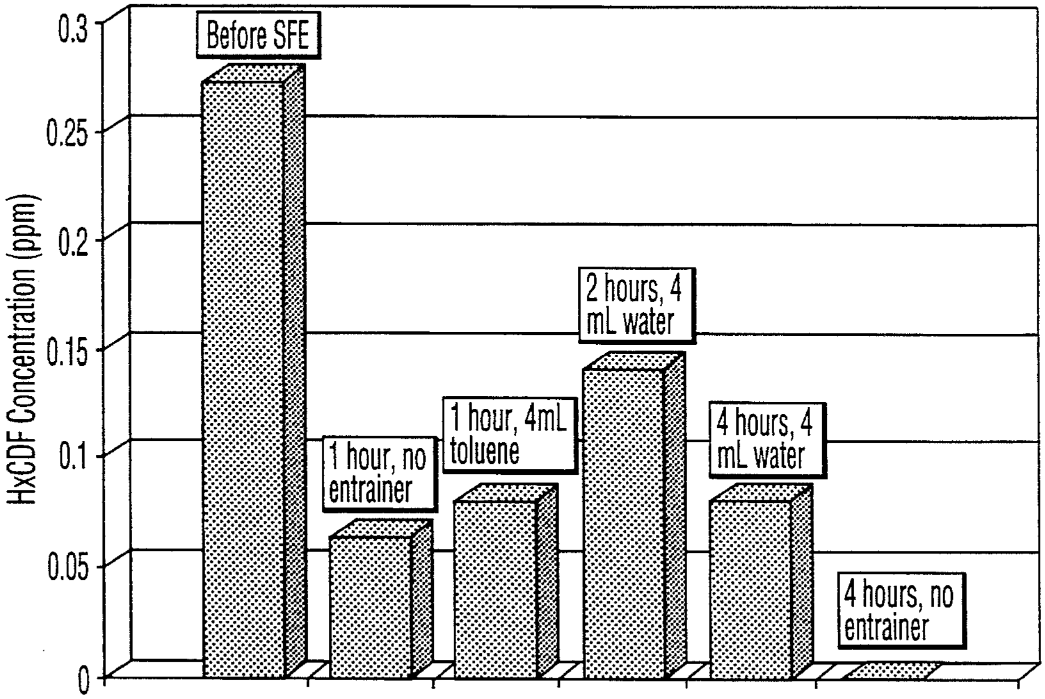
FIG. 12 is a bar graph depicting the change of total hexachlorodibenzofuran concentration after supercritical fluid extraction under various conditions, all extractions being carried out at 50° C. and 250 atmosphere, in which the ordinate is hexachlorodibenzofuran concentration (ppm).

As seen by the bar graphs of FIGS. 5, 6, 7 and 8, the total heptachlorodibenzo-p-dioxin was reduced by SFE more easily than was octachlorodibenzo-p-dioxin. While it is not desired to be limited by theory, it is thought that presumably the heptachlorodibenzo-p-dioxin was more soluble in supercritical carbon dioxide than octachlorodibenzo-p-dioxin. After four hours of extraction without entrainer, the heptachlorodibenzo-p-dioxin was reduced by 94% (FIG. 7). Hexachlorodibenzo-p-dioxins were efficiently reduced by SFE with no hexachlorodibenzo-p-dioxins being detected after one hour of extraction using toluene as the entrainer (FIG. 8).

EXAMPLE 4

Extraction of Furans in the Presence of Entrainers and Fluoride Salts

The extraction of polychlorinated dibenzofurans from the sawdust of a jackpine pole, which was treated in 1974, was also investigated. Although under these experimental conditions, water was the best entrainer for the extraction of pentachlorophenol, it had an adverse effect on polychlorinated dibenzofurans extraction.

The change of total polychlorodibenzofuran concentration after supercritical fluid extraction under various conditions, the change of octachlorodibenzofuran concentration after supercritical fluid extraction under various conditions, and the change of total heptachlorodibenzofuran concentration after supercritical fluid extraction under various conditions, and the change of total hexachlorodibenzofuran concentration after supercritical fluid extraction under various conditions, where all extractions were carried out at 50° C. and 250 atmosphere, were all investigated.

Compared to dioxins, the level of polychlorodibenzofurans was more easily reduced by SFE (FIGS. 9–12). After 4 hours of extraction in the absence of an entrainer, the polychlorodibenzofurans were removed to below the detection limit (<10ppb).

The present invention also provides for the photodegradation of solutions containing toxic organic chemicals. The following examples provide descriptions thereof.

EXAMPLE 5

Photochemical Degradation of Pentachlorophenol

The photochemical degradation of pentachlorophenol was first studied using 1:1 acetonitrile/water (volume) as the solvent. Table 1 below shows the results.

TABLE 1

Photochemical Degradation of Pentachlorophenol ($2 \times 10^{-3}$ M) in 1:1 Acetonitrile/Water (volume) in the Presence of Triethanolamine (0.02M) and Various Sensitizers ($1 \times 10^{-3}$ M)

| Photosensitizer Time (hours) | PCTS | Mix* | Methylene Blue | Protoporphyrin IX |
|---|---|---|---|---|
| | PCP Concentration (ppm) | | | |
| 0 | 500 | 500 | 500 | 500 |
| 1 | 165 | 91.6 | 43.2 | 20 |
| 2 | 71.6 | 28 | 1.2 | 2 |
| 3 | 36 | 1.6 | 0 | 0 |
| 4 | 16 | 0 | 0 | 0 |
| 5 | 8 | 0 | 0 | 0 |
| 6 | 3.2 | 0 | 0 | 0 |
| 7 | 1.6 | 0 | 0 | 0 |

*A mixture of PCTS (phthalocyaninetetrasulfonate), methylene blue, and protoporphyrin IX, each at $3.33 \times 10^{-4}$ M As can be seen from Table 1, pentachlorophenol was rapidly degraded. Only pentachlorophenol and trace amount of tetrachlorophenols were detected by GCMS after acetic anhydride derivatization. Protoporphyrin IX was the most effective photosensitizer, with methylene blue only slightly less effective. Over 99% of the pentachlorophenol was destroyed within two hours using either methylene blue or protoporphyrin IX as sensitizers. The reaction was then repeated in 50% (volume) aqueous ethanol which was cheaper and less toxic than aqueous acetonitrile. Table 2 shows the results of such photochemical degradation.

TABLE 2

Photochemical Degradation of Pentachlorophenol ($2 \times 10^{-3}$ M) in 1:1 Acetonitrile/Water (volume) in the Presence of Triethanolamine (0.02M) and Various Sensitizers ($1 \times 10^{-3}$ M)

| Photosensitizer Time (minutes) | TSPC | Methylene Blue | Protoporphyrin IX |
|---|---|---|---|
| | PCP Concentration (ppm) | | |
| 0 | 500 | 500 | 500 |
| 30 | 229.5 | 110 | 47 |
| 60 | 180 | 5.5 | 1.5 |
| 90 | 139 | 0.25 | 0 |
| 120 | 103 | 0 | 0 |
| 150 | 75.5 | 0 | 0 |
| 180 | 46 | 0 | 0 |

As can be seen from Table 2, the photochemical destruction of pentachlorophenol in this solvent was fast. Within just 1 hour, over 99% of the pentachlorophenol was degraded. Protoporphyrin was again the most effective sensitizer. The differences in the efficiencies of the three sensitizers was probably due to their different extinction coefficients as shown below in Table 3.

TABLE 3

Extinction Coefficient of Three dyes in 1:1 Ethanol/Water (volume)

| Dye | Absorption Maxima (nm) | Extinction Coefficient ($M^{-1}cm^{-1}$) |
|---|---|---|
| Methylene Blue | 660 | $6.8 \times 10^4$ |
| Phthalocyanine- | 637 | $4.0 \times 10^4$ |
| tetrasulfonate | 669 | $3.99 \times 10^4$ |
| Protoporphyrin IX | 378 | $1.48 \times 10^5$ |

Protoporphyrin has an extinction coefficient almost four times larger than that of phthalocyaninetetrasulfonate in 50% ethanol. All three sensitizers absorb light at different wavelengths. It was thought that if the three sensitizers were mixed together, they would absorb light efficiently over a wider range of wavelength and therefore would be more efficient in degrading pentachlorophenol than any individual sensitizers. As can be seen from Table 1, the mixture system containing three sensitizers, each at one third of their regular concentrations, was more effective than phthalocyaninetetrasulfonate, but still less effective than protoporphyrin IX or methylene blue. While it is not desired to be bound by theory, it is believed that this was probably due to the low extinction coefficient of phthalocyaninetetrasulfonate.

The formation of by-products from the photochemical degradation of pentachlorophenol was carefully studied by GCMS analysis of a concentrated extract derivatized with diazomethane. Six products including 2,3,4,6-tetrachlorophenol, tetrachlorohydroquinone, tettrachloracatechol, tetrachlororesorcinol, and dichloromaleic acid were detected. These are shown below.

It was also determined that photochemical degradation of pentachlorophenol under sunlight, through a regular window glass filter, allowed the accumulation of intermediates/products in some cases. In addition to the products identified previously, all three isomers of tetrachlorophenols, six isomers of trichlorophenols, 3,4-dichlorophenol, 2,4-dichlorophenol (and/or 2,5-dichlorophenol, 2,4- and 2,5-dichlorophenols have the same retention time on GC and could not be distinguished), a dichlorodihydroxybenzene and a trichlorodihydroxybenzene were detected, as shown below according to the following scheme.

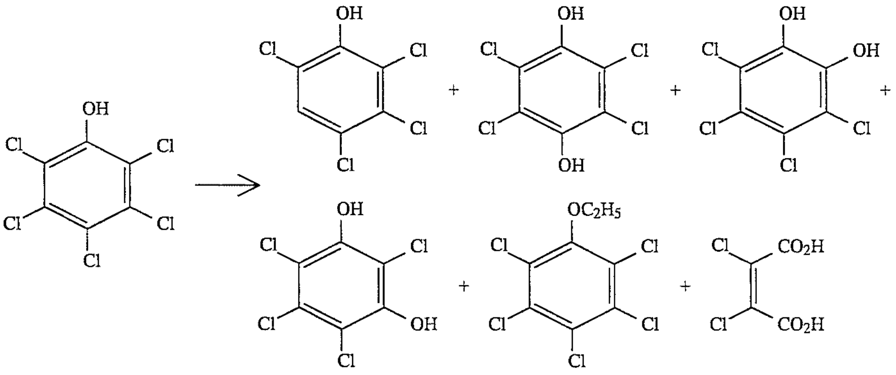

All these products were present only in trace amounts as shown below in Table 4. The identities of these products were confirmed by their mass spectra, and by comparing their GC retention times with those of standards on two different columns (DB-1 and DB-5)

TABLE 4

The yield (%) of some major products from the photochemical degradation of PCP under sunlight or sunlight through a regular window glass filter in the presence of triethanolamine (0.02M) and protoporphyrin or methylene blue ($1 \times 10^{-3}$ M) in 1:1 ethanol/water

| | | Protoporphyrin | | | | Methylene Blue | | | |
|---|---|---|---|---|---|---|---|---|---|
| Time (hours) | | 1 | 2 | 3 | 4 | 1 | 2 | 3 | 4 |
| Light Source | Product* | % yield | | | | | | | |
| sunlight | Tri-CP | 0.003 | 0.004 | 0.006 | 0.005 | 0.0014 | 0.0011 | 0.0010 | 0.001 |
| | Tetra-CP | 0.38 | 0.055 | 0.005 | 0.0025 | 6.0 | 1.58 | 0.075 | 0.0076 |
| | TCC | 1.23 | 0.35 | 0.065 | 0.028 | 1.32 | 0.236 | 0.026 | 0.011 |
| | TCHQ | 0.15 | 0.16 | 0.012 | 0.0005 | 0.24 | 0.26 | 0.20 | 0.0006 |
| | TCR | 0.085 | 0.019 | ND | ND | 0.33 | 0.10 | ND | ND |
| sunlight | Tri-CP | 0.00016 | 0.00075 | 0.001 | 0.0024 | ND | 0.0004 | 0.0005 | 0.0056 |
| through | Tetra-CP | 0.69 | 0.14 | 0.011 | 0.0045 | 3.54 | 1.25 | 0.08 | 0.0052 |
| window | TCC | 0.99 | 0.25 | 0.027 | 0.012 | 1.28 | 0.41 | 0.044 | 0.068 |
| glass | TCHQ | 0.052 | 0.117 | 0.014 | 0.0024 | 0.21 | 0.23 | 0.22 | 0.016 |
| | TCR | 0.069 | 0.0244 | 0.001 | ND | 0.16 | 0.09 | 0.002 | ND |

*Product abbreviations:
Tri-CP: trichlorophenols;
Tetra-CP: tetrachlorophenols;
TCC: tetrachlorocatechol;
TCHQ: tetrachlorohydroquinone;
TCR: tetrachloroesorcinol

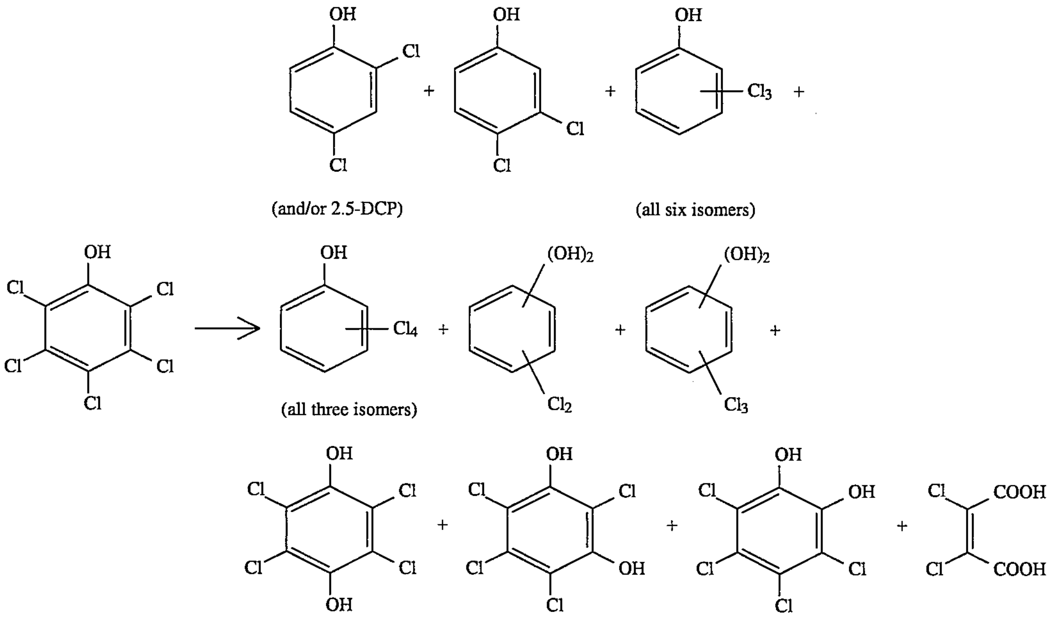

The dichlorodihydroxybenzene and the trichlorodihydroxybenzene were identified only based on their mass spectra, as no standards were available. All other products were positively identified by comparing their mass spectra and their retention times with those of standards on two different GC columns (DB-1 and DB-5). The tetrachlorophenols and tetrachlorohydroquinone, tetrachlorocatechol, and tetrachlororesorcinol were present in much larger quantities under filtered sunlight than those of the reaction under direct sunlight.

Photodegradation of pentachlorophenol in a slurry of pentachlorophenol-containing sawdust in water was also studied using protoporphyrin IX and methylene blue as sensitizers. The results are summarized in Table 5 below.

TABLE 5

Photochemical treatment of sawdust (1 g, 27,000 ppm PCP) in 20 mL 1:1 ethanol/water (volume) in the presence of a sensitizer (1 x $10^{-3}$ M) and triethanolamine (0.02M)

| Time | PCP Concentration (ppm) | | | |
|---|---|---|---|---|
| | Methylene Blue | | Protoporphyrin | |
| (hrs) | Liquid Phase | Sawdust | Liquid Phase | Sawdust |
| 0 | 540 | 27,000 (1,500)* | 667 | 27,000 (1,500) |
| 1 | 897 | — | 536 | — |
| 2 | 702 | — | 237 | — |
| 3 | 170 | — | 107 | — |
| 4 | 53.5 | 948 (517) | 23.2 | 791 (161) |
| 5 | 12.7 | — | 8.3 | — |
| 6 | 6.0 | — | 4.7 | — |
| 7 | 5.5 | — | 6.1 | — |
| 8 | 4.1 | 145 (0) | 4.4 | 115 (0) |

*Data in brackets was the concentration of 2,3,4,6-tetrachlorophenol in ppm

As can be seen from Table 5, pentachlorophenol concentration in both liquid and solid phase decrease rapidly. After eight hours of irradiation, only 4 ppm of pentachlorophenol remained in the liquid phase, and 115–145 ppm of pentachlorophenol remained in the solid phase.

EXAMPLE 6

Photodegradation of Dioxins and Furans

The change in the concentration of polychlorinated dibenzo-p-dioxins and polychlorinated dibenzofurans due to photochemical degradation of pentachlorophenol was investigated. The results are shown below in Table 6.

TABLE 6

Changes in PCDD/PCDF level after photochemical degradation of PCP (0.0300 g) under sunlight for 8 hours in the presence of protoporphyrin IX and triethanolamine

| | Amount of PCDD/PCDF (ng) | | | |
|---|---|---|---|---|
| | Technical PCP | | PURE PCP | |
| | Control | Photo-degradation | Control | Photo-degradation |
| HxCDD | nd* | nd | nd | nd |
| HpCDD | 1,700 | 460 | nd | nd |
| OCDD | 48,300 | 12,660 | 5.83 | 3.42 |
| HxCDF | 229 | 143 | nd | nd |
| HpCDF | 2,100 | 558 | nd | nd |
| OCDF | 4,800 | 820 | 1.1 | 0.47 |

*nd = not detected
Product Abbreviations:
PCP = pentachlorophenol
PCDF = polychlorinated dibenzofurans
OCDD = octachlorodibenzo-p-dioxin
HpCDD = heptachlorodibenzo-p-dioxin
HxCDD = hexachlorodibenzo-p-dioxin
PCDD = polychlorinated benzo-p-dioxins
OCDF = octachlorodibenzofurans
HpEDF = heptachlorodibenzofurans
HxCDF = hexachlorodibenzofurans It can be seen from Table 6 that the levels of polychlorinated dibenzo-p-dioxins and polychlorinated dibenzofurans decreased in technical pentachlorophenol dramatically after photochemical oxidation, with octachlorodibenzo-p-dioxin reduced by over 70%. After photochemical oxidation of pure pentachlorophenol, the levels of octachlorodibenzo-p-dioxin also decreased as shown in Table 6.

Photochemical treatment of toxic wastes is attractive, in that it uses a free energy source, sunlight. A disadvantage of this process is that the reactions are often slow, because only a few contaminants can strongly absorb sunlight. Pentachlorophenol has a weak absorption peak at around 330 nm, which is at the high energy end of sunlight spectrum and is degraded slowly. The use of photosensitizers and amines has been proved successful. Both pentachlorophenol and polychlorinated dibenzo-p-dioxin/polychlorinated dibenzofuran contaminants are degraded rapidly without the formation of more toxic or more recalcitrant by-products. The trace amounts of products/intermediates are more easily mineralized chemically or biologically than pentachlorophenol. Dichloromaleic acid, tetrachlorocatechol, tetrachlororesorcinol, tetrachloroquinone, and lower chlorophenols have been identified as pentachlorophenol photodegradation products. Tetrachlorohydroquinone was also detected. The formation of a number of dimeric and trimeric products during photodegradation of aqueous sodium pentachlorophenate solutions have previously been reported by others. However, no such compounds were formed under the reactions described above. In the present examples, it was found that the presence of photosensitizers and triethanolamine did not result in an increase in polychlorinated dibenzo-p-dioxin/polychlorinated dibenzofuran concentration. While it is not desired to be limited by theory, it is thought that this was probably because polychlorinated dibenzo-p-dioxins and polychlorodibenzofurans were degraded at a rate faster than their formation.

While it is not desired to be limited by theory, it is thought that the photosensitizers and triethanolamine apparently remained unchanged after the photochemical reaction. As a result, when pentachlorophenol-containing sawdust is treated as a slurry, the majority of the sensitizer and triethanolamine remains in the liquid phase and thus can be reused.

It was previously found that in the use of solar irradiation for treating soil contaminated with wood preservative wastes in solid phase, both pentachlorophenol and polycyclic aromatic hydrocarbons were degraded. The presence of anthracene, a polycyclic aromatic hydrocarbon component of the oil, enhanced the degradation of other components.

OPERATION OF PREFERRED EMBODIMENTS

The SFE of pentachlorophenol-containing heartwood of a jackpine pole with carbon dioxide alone was very inefficient. The addition of water as an entrainer reduced the pentachlorophenol concentration by 60% in 1 hour. The addition of sodium fluoride to water improved the extraction efficiency of jackpine sapwood, with the pentachlorophenol content being reduced by 50% in the first hour of extraction. Extraction of the remaining pentachlorophenol was more difficult, and 15% pentachlorophenol remained after 4 hours of extraction.

It has thus been found that supercritical carbon dioxide extraction is a promising technique for the removal of pentachlorophenol from treated poles. The pentachlorophenol concentration was easily reduced, allowing the wood to be treated with microorganisms for complete removal of toxic chlorophenols. While SFE represents only one pretreatment process according to one aspect of this invention before bioremediation using photodegradation according to another aspect of this invention, it has several advantages, including easy removal of chlorophenols and other contaminants, e.g., oil and the extremely toxic polychlorinated dibenzo-p-dioxins and polychlorinated dibenzofurans.

The process used involves the extraction of pentachlorophenol, contaminants (including polychlorinated dibenzo-p-dioxins and polychlorinated dibenzofurans) and the oil solvent from the treated wood poles after processing of the roundwood into particulate matter (i.e., chips, or flakes, or thin sheets). The gas used was carbon dioxide together with entrainers, e.g., water, methanol, ethanol, propanol, isopropanol, acetone, tetrahydrofuran, dimethylformamide or dimethylsulfoxide, as well as alkali metal fluorides, e.g., sodium fluoride, potassium fluoride and lithium fluoride. While it is not desired to be limited by theory, it is thought that the water was helpful by causing the wood cell wall to swell thereby improving access to the trapped pentachlorophenol. While it is not desired to be limited by theory, it is thought that the methanol and other agents, e.g., ethanol, propanol and acetone, behaved similarly. While it is not desired to be limited by theory, it is thought that the sodium fluoride may function by breaking the hydrogen bonding of the pentachlorophenol or impurities in the wood thereby enhancing their recovery. Other agents which break such hydrogen bonding may alternatively be used. Examples of possible other such agents include the following: potassium fluoride and lithium fluoride.

The present invention thus shows that supercritical carbon dioxide extraction, in conjunction with entrainers and hydrogen-bond-treating agents, is a promising technique for the removal of pentachlorophenol from treated poles. The pentachlorophenol concentration was easily reduced, allowing the wood to be treated with microorganisms for complete removal of toxic chlorophenols. While SFE represents only one pretreatment method before final degradation of contaminants, it has several advantages. Among such advantages are easy removal of chlorophenols and other contaminants, e.g., oil, and the extremely toxic polychlorinated dibenzo-p-dioxins and polychlorinated dibenzofurans. Photodegradation may be used according to this invention to degrade toxic organic chemicals from solutions thereof, regardless of the source of the contaminanted solutions. Based upon current knowledge, bioremediation alone is not expected to be able to detoxify all the polycyclic aromatic hydrocarbons, polychlorinated dibenzo-p-dioxins and polychlorinated dibenzofurans. Substantially-complete decontamination of pentachlorophenol-treated poles, desirably includes the SFE treatment of one aspect of this invention followed by the photodegradation according to another aspect of this invention using techniques as described in the present application.

In addition the photodegradation of solutions of such contaminants has also been provided.

CONCLUSION

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

We claim:

1. A process for extracting organic toxic contaminants including pentachlorophenol, polychlorinated dibenzo-p-dioxins, and polychlorinated dibenzofurans, from wood which process comprises: extracting said wood with a supercritical fluid, an entrainer having wood swelling properties and an agent to break the hydrogen bond between the organic toxic contaminants and the wood, at conventional supercritical fluid extraction temperatures and pressures, thereby to extract said contaminants from said wood.

2. The process of claim 1 wherein said supercritical fluid is carbon dioxide.

3. The process of claim 1 wherein said entrainer is an agent selected from the group consisting of water, methanol, ethanol, propanol, isopropanol, toluene, acetone, tetrahydrofuran, dimethylfurmamide and dimethylsulfoxide.

4. The process of claim 3 wherein said entrainer is water.

5. The process of claim 3 wherein said entrainer is methanol.

6. The process of claim 2 wherein said entrainer is water.

7. The process of claim 2 wherein said entrainer is methanol.

8. The process of claim 1 wherein said hydrogen-bond-breaking agent is an alkali metal fluoride.

9. The process of claim 8 wherein said alkali metal fluoride is selected from the group consisting of lithium fluoride, potassium fluoride and sodium fluoride.

10. The process of claim 2 wherein said hydrogen-bond-breaking agent is an alkali metal fluoride selected from the group consisting of lithium fluoride, potassium fluoride and sodium fluoride.

11. The process of claim 10 wherein said alkali methal fluoride is sodium fluoride.

12. The process of claim 6 wherein said hydrogen-bond-breaking agent is sodium fluoride.

13. The process of claim 7 wherein said hydrogen-bond-breaking agent is sodium fluoride.

14. The process of claim 1 including the step of reducing the size of said wood by comminuting said wood before said extraction step.

15. The process of claim 1 including the step of reducing the size of said wood by chipping said wood before said extraction step.

16. The process of claim 1 including the step of reducing the size of said wood by forming flakes from said wood before said extraction step.

17. The process of claim 1 including the step of producing segments from outer sapwood of treated utility poles and reducing said segments to flakes before said extraction step.

18. The process of claim 1 including the step of producing thin sheets of wood from outer sapwood of treated utility poles before said extraction step.

19. A process for extracting organic toxic contaminants including pentachlorophenol, polychlorinated dibenzo-p-dioxins, and polychlorinated dibenzofurans, from wood and the subsequent photodegradation of the reaction products which process comprises: extracting said wood with a supercritical fluid, an entrainer having wood swelling properties and an agent to break the hydrogen bond between the organic toxic contaminants and the wood, at conventional supercritical fluid extraction temperatures and pressures; and exposing, in a slurry of said extracted wood, or in a liquid solvent resulting from said extractions, said contaminants to radiation including UV or sunlight, in the presence of a photosensitizing amount of a suitable photosensitizer.

20. The process of claim 19 wherein said radiation comprises direct sunlight.

21. The process of claim 19 wherein said suitable photosensitizer is methylene blue.

22. The process of claim 19 wherein said photosensitizer is a porphyrin.

23. The process of claim 22 wherein said porphyrin is protoporphyrin IX.

24. The process of claim 19 wherein said suitable photosensitizer is a phthalocyanine.

25. The process of claim 19 wherein the irradiation takes place in the presence of an amine.

26. The process of claim 25 wherein said amine is triethanolamine.

27. The process of claim 19 wherein said solvent is a water-miscible solvent.

28. The process of claim 19 wherein said water-miscible solvent for said solvent phase is selected from the group consisting of acetonitrile, methanol and ethanol.

* * * * *